US00PP24902P3

(12) United States Plant Patent
Egger

(10) Patent No.: US PP24,902 P3
(45) Date of Patent: Sep. 16, 2014

(54) ***SEDUM* PLANT NAMED 'DESERT BLACK'**

(50) Latin Name: *Sedum telephium (Hylotelephium telephium)*
Varietal Denomination: Desert Black

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 74 days.

(21) Appl. No.: 13/815,310

(22) Filed: Feb. 19, 2013

(65) Prior Publication Data

US 2014/0237693 P1 Aug. 21, 2014

(51) Int. Cl.
*A01H 5/00* (2006.01)

(52) U.S. Cl.
USPC ..... Plt./479

(58) Field of Classification Search
USPC ..... Plt./479
See application file for complete search history.

*Primary Examiner* — Annette Para
(74) *Attorney, Agent, or Firm* — Klarquist Sparkman LLP

(57) ABSTRACT

A new and distinct hybrid of *Sedum* plant substantially as shown and described, characterized by medium oblong dark brown leaves with entire margins, high crown count, short stems of dark maroon, a low, clumping habit, and excellent vigor.

1 Drawing Sheet

Botanical denomination: *Sedum telephium* (*Hylotelephium telephium*).
Variety designation: 'Desert Black'.

BACKGROUND OF THE INVENTION

The present invention relates to a new and distinct cultivar of *Sedum* and given the cultivar name of 'Desert Black'. *Sedum* is in the family Crassulaceae. *Sedum* 'Desert Black' is the result of a planned breeding project to produce short dark leaf *Sedum telephium* (*Hylotelephium telephium*) with high crown counts. The new cultivar originated from an open pollinated cross of *Sedum telephium* 8-4, a proprietary, unpatented plant.

Compared to *Sedum telephium* 8-4, the new cultivar is smaller with darker, smaller leaves.

Compared to *Sedum* 'Chocolate Drop' (U.S. Plant Pat. No. 22,866), the new variety has a broader habit with a bigger crown faster and with leaves that are oblong and black rather than oval and red brown.

SUMMARY OF THE INVENTION

This new and unique *Sedum* is distinguished by:

1. medium oblong dark brown leaves with entire margins,
2. high crown count,
3. short stems of dark maroon,
4. a low, clumping habit, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the spring leaves of a two-year-old *Sedum* 'Desert Black' growing outside in late May in Canby, Oreg.

FIG. 2 shows the same plant in bloom growing in the garden in mid-August in Canby, Oreg.

DETAILED PLANT DESCRIPTION

The following is a detailed description of the new *Sedum* hybrid based on observations of two-year-old specimens grown in the trial field in full sun under typical outdoor conditions in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on *The Royal Horticultural Society Colour Chart*, $5^{th}$ edition.

Plant:

*Type.*—Herbaceous perennial.
*Hardiness.*—USDA Zone 4 to 9.
*Size.*—31 cm tall from the ground to the top of the inflorescence and 45 cm wide.
*Habit.*—Erect, clumping.
*Vigor.*—Excellent.

Stem:

*Number.*—About 15.
*Size.*—29 cm long and 9 mm wide.
*Internode length.*—10 mm to 20 mm long.
*Color.*—Greyed Purple 187B.
*Texture.*—Succulent.
*Surface.*—Glabrous, glossy.

Leaf:

*Type.*—Simple.

*Arrangement.*—Whorls.

*Shape.*—Oblong.

*Apex.*—Obtuse.

*Base.*—Cuncate.

*Venation.*—Pinnate.

*Margins.*—Entire to shallowly serrate.

*Blade size.*—Grows to 7 cm long and 2.5 cm wide.

*Surface.*—Glabrous.

*Petiole.*—Leaves sessile.

*Leaf color.*—Spring topside closest to Greyed Purple N186B with the main vein Greyed Purple N186C on top and bottom side, bottom side closest to Brown 200B; summer topside closest to Brown 200A with vein Greyed Purple 187A; bottom side closest to Brown N200B with vein Greyed Purple 187A.

Inflorescence:

*Type.*—Terminal, corymbose.

*Number of flowers.*—About 1000 per stem (increases with stem size).

*Pedicels.*—1 mm to 3 mm long, 1 mm wide, glabrous, Greyed Purple 187A.

*Peduncle.*—6 cm to 12 cm tall and grows to 5 mm wide, Greyed Purple N186C, succulent, glabrous.

*Size.*—Grows to 17 cm deep and 19 cm wide.

*Bloom period.*—August through September in Canby, Oreg.

Flower bud:

*Size.*—2 mm wide, 5 mm deep.

*Description.*—Ovoid.

*Color.*—Red Purple 70A.

Flower:

*Type.*—Complete, actinomorphic.

*Shape.*—Stellate.

*Size.*—3 mm deep and 6 mm wide.

*Corolla description.*—3 mm deep and 6 mm wide, 5 petals, each lanceolate, 4 mm long and 1.5 mm wide, margins entire, tip acuminate, glabrous on both sides, topside Purple 70C, bottom side Purple 70B.

*Calyx description.*—1.5 mm deep and 2 mm wide, campanulate, 5 lobes, divided to the base, margins entire, tip acute, glabrous, Greyed Purple N187A on both sides.

*Stamen description.*—10 in number, 3 mm long, filaments 3 mm long, Greyed Purple 186D, anthers Yellow 11B, no pollen, male sterile.

*Pistil description.*—5 separate prominent carpels, each 2.5 mm deep and 1 mm wide, Greyed Purple N186D; style 0.5 mm long and Greyed Purple 187A, stigma Greyed Purple 187A.

*Fragrance.*—None.

*Lastingness.*—Each stem lasts up to a month.

Fruit: None.

Seed: No seed produced.

Disease and pest resistance or tolerance: Pest and disease resistance are typical for this type of *Sedum*. No known resistances.

I claim:

1. A new and distinct hybrid of *Sedum* plant as herein illustrated and described.

* * * * *

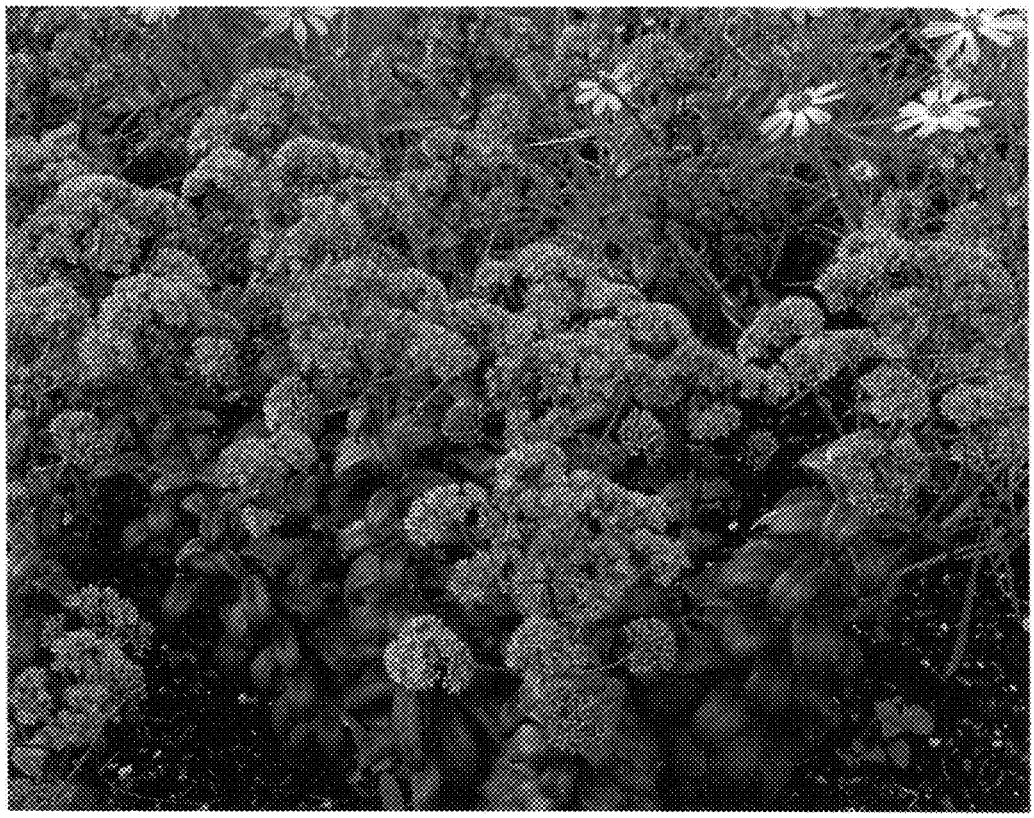

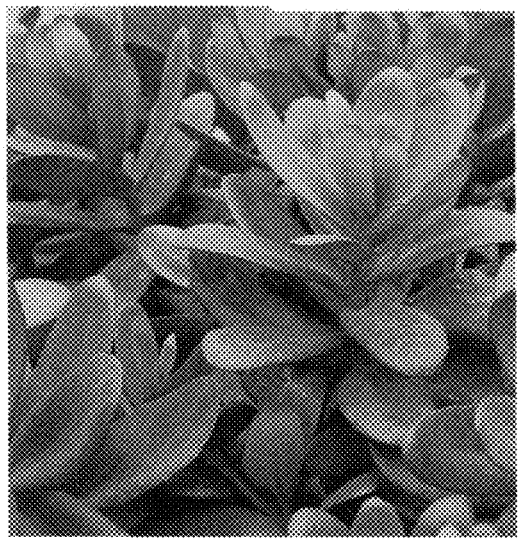
FIG. 1 on left
FIG. 2 below.